(12) United States Patent
Wernitz

(10) Patent No.: US 8,607,633 B2
(45) Date of Patent: Dec. 17, 2013

(54) MEASURING SYSTEM FOR RESONANT FREQUENCY MEASUREMENTS ON DISC BRAKE PADS

(75) Inventor: Boris Wernitz, Glinde (DE)

(73) Assignee: Honeywell Bremsbelag GmbH, Glinde (DE)

( * ) Notice: Subject to any disclaimer, the term of this patent is extended or adjusted under 35 U.S.C. 154(b) by 198 days.

(21) Appl. No.: 13/253,278

(22) Filed: Oct. 5, 2011

(65) Prior Publication Data

US 2012/0085172 A1 Apr. 12, 2012

(30) Foreign Application Priority Data

Oct. 7, 2010 (DE) .......................... 10 2010 042 170

(51) Int. Cl.
*G01N 29/14* (2006.01)
(52) U.S. Cl.
USPC .............................................. 73/579; 73/587
(58) Field of Classification Search
USPC ......... 73/579, 593, 649, 659, 660, 11.01, 587
See application file for complete search history.

(56) References Cited

U.S. PATENT DOCUMENTS

| | | | | |
|---|---|---|---|---|
| 5,029,806 A | * | 7/1991 | Huo-Lien et al. | 251/14 |
| 5,363,939 A | * | 11/1994 | Catlin | 180/291 |
| 5,931,051 A | * | 8/1999 | Ott | 74/574.4 |
| 6,105,422 A | * | 8/2000 | Pollock et al. | 73/121 |
| 6,662,641 B2 | * | 12/2003 | Scorteanu et al. | 73/121 |
| 7,391,306 B2 | * | 6/2008 | Dufournier | 340/442 |
| 7,422,294 B2 | * | 9/2008 | Yamamoto | 303/122.12 |
| 7,603,247 B2 | * | 10/2009 | Isono et al. | 702/116 |
| 7,850,255 B2 | * | 12/2010 | Kawahara et al. | 303/122.1 |

FOREIGN PATENT DOCUMENTS

| | | | |
|---|---|---|---|
| DE | 004034463 A1 | * | 5/1992 |
| JP | 06117467 A | * | 4/1994 |
| JP | 2000055893 | * | 2/2000 |

* cited by examiner

*Primary Examiner* — J M Saint Surin
(74) *Attorney, Agent, or Firm* — Alston & Bird LLP

(57) ABSTRACT

A system is provided for measuring the resonant frequencies on disc brake pads. The system includes a data recording apparatus and a measuring device in the form of a sensor system. In order to record a maximum number of resonant frequencies, the sensor system consists of two or more microphones.

12 Claims, 1 Drawing Sheet

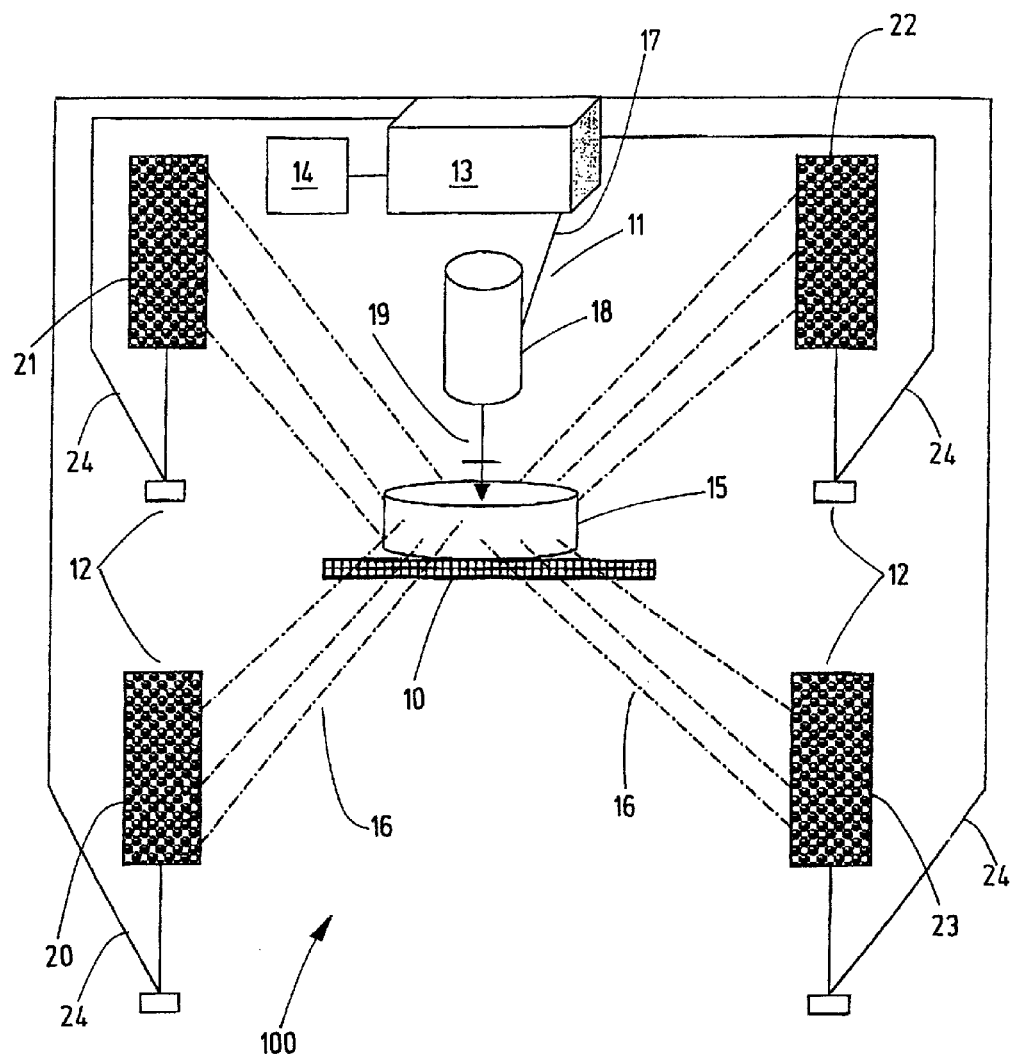

MEASURING SYSTEM FOR RESONANT FREQUENCY MEASUREMENTS ON DISC BRAKE PADS

The invention relates to a measuring system for resonant frequency measurements on disc brake pads with a data recording apparatus and a measuring device comprising a sensor system.

In addition the invention relates to a method for measuring resonant frequencies on disc brake pads by using microphones.

Measuring systems of the kind mentioned in the beginning are commonly known and familiar to an expert in the art.

Resonant frequencies represent important characteristic variables for describing the vibrational behaviour of disc brake pads. Variables with influence upon the resonant frequencies, i.e. on the vibrational behaviour of disc brake pads are, for example, elasticities, compressibility, density, mass, porosity, hardness, thickness, geometry such as the chamfer of disc brake pads, and the damping characteristics of disc brake pads.

When disc brake pads are checked, if they are of roughly the same constructional size, the resonant frequency can be used to draw conclusions as to the material from the disc brake pads are manufactured. In addition the resonant frequencies can be used for checking to what extent the disc brake pads have the same properties.

Measuring systems of the kind mentioned in the beginning therefore serve in particular to check the material properties of disc brake pads for the purposes of quality assurance. Measuring in the measuring system is carried out in such a way that initially the object to be measured, i.e. the disc brake pad, is made to vibrate by imparting a knock. This stimulation may, for example, be effected by hitting it with a hammer. The advantage of the knock consists in that all vibrations over a wide frequency range are simultaneously stimulated. Preferably the disc brake pad is placed on a soft foam base and thus performs an approximately free vibration since due to the foam mounting the vibrations in the environment of the disc brake pad are decoupled. What is also important is the defined placement of the measuring object, i.e. the disc brake pad, on the foam base. The reason for this is the accuracy of repetition of the measurement, since for a variation in the placement the resonant frequencies can be stimulated with different intensities.

The aim of carrying out the measurement is to obtain a neutral response regarding the vibrational behaviour of the disc brake pad. To this end the auto-correlation function of the system response is mathematically calculated which, if interpreted in a visual way, supplies information on how strongly the disc brake pad responds to a stimulation force for the frequency f. At the so-called resonant frequencies fc the object to be measured, i.e. the disc brake pad, gives a particularly high response (vibrational amplitude), the auto-correlation function has pronounced functional precepts at these points.

In order record the vibrations, contactless measuring by microphone is known from the state of the art. Contactless microphone measuring consists in that only one microphone records the vibrations of the stimulated disc brake pad. Contactless microphone measuring using only one microphone has the advantage, as compared to measuring by means of other sensors such as with acceleration receptors, that the resonant frequencies and vibrational patterns of the disc brake pad are not influenced by the sensor mass. Contactless microphone measuring as known from the state of the art has proved to be insufficient insofar as only one limited recording can be made by means of one microphone from the wide frequency range, since in the immediate spatial environment of the microphone the forming of nodal lines in the sound field can not be excluded.

It is therefore the object of the invention to further develop a measuring system of the kind mentioned in the beginning, which can record a large number of resonant frequencies.

This requirement is met by the features of claim 1. Advantageous designs of the invention can be derived from the sub-claims.

The invention provides for the sensor system consisting of two or more microphones.

The core idea of the invention is to record as many resonant frequencies as possible from the wide frequency range by using several microphones. To this end the microphones may be positioned in various ways in relation to the object to be measured, i.e. the disc brake pad. For example, the distances between the object to be measured, i.e. the disc brake pad, and the respective microphones may vary, resulting in the microphones being staggered in relation to each other in direction of the disc brake pad. A further configuration of the microphones in the sound field may be implemented in such a way that all microphones are placed in a circular manner about the disc brake pad. Preferably the placement of the microphones should be adapted to the emission characteristic of the sound field.

The advantage of the invention should be seen in the fact that several microphones, i.e. two or more microphones, arranged in the sound field about the disc brake pad ensure that the resonant frequencies to be measured are recorded at different points in the sound field by means of the microphones so that a more effective avoidance of nodal lines within the sound field expanding with regard to both time and space is possible. This again results in a larger stability of the measurement and a high measuring and repetition accuracy.

In order to stimulate the disc brake pad by means of a stimulation force an advantageous design of the invention provides for the measuring device to comprise a pulse-stimulating device. Advantageously the disc brake pad and the pulse-stimulating device are arranged in relation to each other in such a way that an unequivocal and easily reproducible adjustability of the stimulating position is possible. A practical variant of the invention provides for the pulse-stimulating device to have the form of a hammer.

In order to enable the disc brake pad and vibration pairs to be decoupled from the base (table or similar), an object holder is advantageous for the disc brake pad. Preferably the object holder consists of foam with a thickness of 25 kg/cm$^3$ and a resistance to crushing of 3.5 hPa. Conveniently the disc brake pad may also be arranged on an object holder the density of which lies between 10 and 1000 kg/cm$^3$. Alternatively the density may be between 400 and 1200 kg/m$^3$.

Further the invention provides for a method for measuring resonant frequencies of disc brake pads by means of microphone measuring, wherein the resonant frequencies are recorded by two or more microphones. Preferably the disc brake pad is stimulated by a knock and decoupled from its environment. Knocking may be effected by a hammer.

The present application also describes a computer program for a computer unit which is part of the data recording apparatus, wherein the computer program contains an algorithm, which is run as part of the data recording process.

In addition the invention provides for the use of two or more microphones for measuring the resonant frequencies of a disc brake pad.

The invention will now be explained with reference to the drawing, in which

FIG. 1 shows a measuring system according to the invention.

In FIG. 1 a measuring system according to the invention is shown which is referenced with 100.

The measuring system 100 is used to measure resonant frequencies on disc brake pads.

The measuring system 100 essentially comprises two components. The first component is the measuring device which is composed of an object holder 10, a pulse-stimulating device 11 and a sensor system 12. The data recording apparatus 13 is the second component, which comprises a measuring computer, a frequency analyser and a computer unit referenced with 14.

The object holder 10 is comprised of a base made from plastic foam, on which the disc brake pad 15 is mounted in a defined position. The plastic foam thus serves as support for the disc brake pad and is active so as to decouple the sound from the body on which the plastic foam rests. The pulse-stimulating device 11 is arranged above the disc brake pad 15, i.e. on the side of the disc brake pad 15 facing away from the object holder 10, wherein the pulse-stimulating device 11 is present in the form of a hammer device 18. The disc brake pad 15 is stimulated to vibrate by giving it a knock with the hammer 18 indicated in FIG. 1 by an arrow 19. This knock 19 has the effect of causing vibrations in the disc brake pad 15 over a wide frequency range. These vibrations and the associated resonant frequencies are recorded by the measuring system 100.

To this end the sensor system 12, in an inventive way, consists of more than one microphone. In the embodiment of the measuring system 100 according to the invention shown in FIG. 1 the measuring system 100 comprises microphones 20, 21, 22, 23 which are arranged about the disc brake pad 15. The arrangement of several microphones 20, 21, 22, 23, which are preferably distanced no more than 50 cm from the disc brake pad, has the advantage, among others, that the formation of nodes, i.e. longitudinal waves, in the sound field 16 can be reduced.

Preferably the microphones 20, 21, 22, 23 are aligned in the room and/or surrounded by walls not shown in FIG. 1, in such a way as to ensure low-interference recording.

The microphones 20, 21, 22, 23 are connected via a connection 24 to the data recording apparatus 13, which records and evaluates the response of the disc brake pad 15 by means of a measuring computer and a frequency analyser. The data recording apparatus 13 can utilise the connection 17 to also control the pulse-stimulating device 11 in principle. The computer unit 14 associated with the data recording apparatus 13 is also instrumental in recording the measured data, controlling the measuring sequence and evaluating the measured data, as it comprises a computer program containing an algorithm which is run as part of recording the data, controlling the measuring sequences and evaluating the measured data.

LIST OF REFERENCE SYMBOLS

100 measuring system
10 object holder
11 pulse-stimulating device
12 sensor system
13 data recording apparatus
14 computer unit
15 disc brake pad
16 sound field
17 connection
18 hammer device
19 knock of the hammer device
20 microphone
21 microphone
22 microphone
23 microphone
24 connection

The invention claimed is:

1. A measuring system for carrying out resonant frequency measurements on a disc brake pad, the measuring system comprising a data recording apparatus and a measuring device comprising a sensor system, the sensor system including two or more microphones arranged for measuring resonant frequencies at respectively different points in a sound field emitted by the disc brake pad, the two or more microphones being arranged so as to reduce formation of longitudinal waves in the sound field.

2. The system according to claim 1, wherein the measuring device comprises a pulse-stimulating device.

3. The system according to claim 2, wherein the pulse-stimulating device comprises a hammer.

4. The system according to claim 2, wherein the pulse-stimulating device is connected to the data recording apparatus.

5. The system according to claim 1, wherein the disc brake pad is arranged on an object holder having a density of 400 to 1200 kg/m$^3$.

6. The system according to claim 1, wherein the disc brake pad is arranged on an object holder having a density of 10 to 1000 kg/m$^3$.

7. The system according to any one of claims 1-6, wherein the arrangement of the microphones is adapted to the emission characteristic of the sound field.

8. The system according to any one of claims 1-3, 5 and 6 wherein a distance of the disc brake pad to the microphones is no more than 50 cm.

9. A method for measuring the resonant frequencies of a disc brake pad by means of microphone measuring, wherein the resonant frequencies are recorded by two or more microphones arranged for measuring the resonant frequencies at respectively different points in a sound field emitted by the disc brake pad, the two or more microphones being arranged so as to reduce formation of longitudinal waves in the sound field.

10. The method according to claim 9, wherein the disc brake pad is stimulated by a knock.

11. The method according to claim 10, wherein the knock is effected by a hammer.

12. The method according to claim 9, wherein the disc brake pad is decoupled from vibrations in its environment.

* * * * *